(12) United States Patent
Kuo

(10) Patent No.: US 10,925,690 B2
(45) Date of Patent: Feb. 23, 2021

(54) FILLING UNDERCUT AREAS OF TEETH RELATIVE TO AXES OF APPLIANCE PLACEMENT

(71) Applicant: Align Technology, Inc., San Jose, CA (US)

(72) Inventor: Eric E. Kuo, San Jose, CA (US)

(73) Assignee: Align Technology, Inc., San Jose, CA (US)

( * ) Notice: Subject to any disclaimer, the term of this patent is extended or adjusted under 35 U.S.C. 154(b) by 267 days.

(21) Appl. No.: 16/185,512

(22) Filed: Nov. 9, 2018

(65) Prior Publication Data

US 2019/0076215 A1 Mar. 14, 2019

Related U.S. Application Data

(63) Continuation of application No. 15/182,171, filed on Jun. 14, 2016, now Pat. No. 10,123,852, which is a continuation of application No. 13/680,888, filed on Nov. 19, 2012, now Pat. No. 9,364,296.

(51) Int. Cl.
| | |
|---|---|
| *A61C 7/00* | (2006.01) |
| *A61C 7/08* | (2006.01) |
| *A61C 9/00* | (2006.01) |
| *G16H 50/50* | (2018.01) |
| *G06F 19/00* | (2018.01) |
| *G06F 30/00* | (2020.01) |

(52) U.S. Cl.
CPC .............. *A61C 7/002* (2013.01); *A61C 7/08* (2013.01); *A61C 9/004* (2013.01); *A61C 9/0046* (2013.01); *G06F 19/00* (2013.01); *G16H 50/50* (2018.01); *G06F 30/00* (2020.01)

(58) Field of Classification Search
None
See application file for complete search history.

(56) References Cited

U.S. PATENT DOCUMENTS

| | | | |
|---|---|---|---|
| 2004/0166462 A1* | 8/2004 | Phan ................... | B33Y 50/02 433/24 |
| 2004/0209218 A1* | 10/2004 | Chishti ................ | A61C 7/36 433/6 |
| 2005/0186524 A1* | 8/2005 | Abolfathi ............ | A61C 7/10 433/7 |
| 2006/0003292 A1* | 1/2006 | Lauren ................ | A61C 7/00 433/215 |
| 2006/0263739 A1 | 11/2006 | Sporbert et al. | |
| 2009/0248184 A1* | 10/2009 | Steingart ............ | G06F 3/016 700/98 |

\* cited by examiner

*Primary Examiner* — Cedric Johnson
(74) *Attorney, Agent, or Firm* — Shay Glenn LLP

(57) ABSTRACT

The present disclosure provides computing device implemented methods, computing device readable medium, and molds for filling undercut areas of teeth relative to an axis of placement. Filling undercut areas of teeth relative to an axis of placement can include calculating an undercut area of a tooth relative to an axis of placement of part of a dental appliance over a number of teeth and a height of contour that is defined based on the axis of placement. Filling undercut areas of teeth relative to an axis of placement can also include filling in a part of the undercut area of the tooth with a virtual filler wherein the undercut is filled to within a threshold distance from the tooth that is defined relative to the axis of placement and the height of contour.

20 Claims, 6 Drawing Sheets

582⤦

```
┌─────────────────────────────────────────────────────┐
│ CREATING A SET OF MOLDED TEETH FROM A DIGITAL       │～584
│ MODEL OF A NUMBER OF TEETH OF A PATIENT             │
└─────────────────────────────────────────────────────┘
                          │
┌─────────────────────────────────────────────────────────────┐
│ ADDING A FILLER MATERIAL TO A FIRST NUMBER OF THE MOLDED    │
│ TEETH AMONG THE SET OF MOLDED TEETH, WHEREIN THE FILLER     │～586
│ MATERIAL IS LOCATED IN AN UNDERCUT AREA OF THE FIRST NUMBER │
│ OF MOLDED TEETH RELATIVE TO AN AXIS OF PLACEMENT OF A       │
│ DENTAL APPLIANCE OVER THE NUMBER OF TEETH                   │
└─────────────────────────────────────────────────────────────┘
```

```
┌─────────────────────────────────────────────────────┐
│ CREATING A SET OF MOLDED TEETH FROM A DIGITAL       │～585
│ MODEL OF A NUMBER OF TEETH OF A PATIENT             │
└─────────────────────────────────────────────────────┘
                          │
┌─────────────────────────────────────────────────────────────┐
│ ADDING AN ARTIFICIAL UNDERCUT TO A FIRST NUMBER OF THE      │
│ MOLDED TEETH AMONG THE SET OF MOLDED TEETH, WHEREIN THE     │
│ ARTIFICIAL UNDERCUT IS LOCATED IN AN UNDERCUT AREA OF THE   │～587
│ FIRST NUMBER OF MOLDED TEETH RELATIVE TO AN AXIS OF         │
│ PLACEMENT OF A DENTAL APPLIANCE OVER THE NUMBER OF TEETH    │
└─────────────────────────────────────────────────────────────┘
```

FILLING UNDERCUT AREAS OF TEETH RELATIVE TO AXES OF APPLIANCE PLACEMENT

PRIORITY INFORMATION

The present application is a continuation of U.S. patent application Ser. No. 15/182,171, filed Jun. 14, 2016 and issued as U.S. Pat. No. 10,123,852 on Nov. 13, 2018, which is a continuation of U.S. patent application Ser. No. 13/680,888, now U.S. Pat. No. 9,364,296, filed on Nov. 19, 2012, the contents of which are incorporated herein by reference.

BACKGROUND

The present disclosure is related generally to the field of dental treatment. More particularly, the present disclosure relates to modifying digital images of teeth to improve fit of dental appliances made using the images.

Dental treatments can involve repositioning misaligned teeth and changing bite configuration for improved cosmetic appearance and dental function. Orthodontic repositioning can be accomplished, for instance, through a dental process that uses one or more removable tooth-positioning appliances for realigning teeth.

Such appliances may utilize a shell of material having resilient properties, referred to as an "aligner" that generally conforms to a patient's teeth but is slightly out of alignment with the then current tooth configuration. Placement of an appliance over the teeth can provide controlled forces in specific locations to gradually move the teeth into a new configuration. The appliances can be semi-rigid, allowing for flexing of the appliances as the appliance is placed over the teeth of a patient.

Placement of the appliance over the teeth can be affected by an undercut area of a tooth of a patient. An undercut area of a tooth can include an area of a tooth below a widest part of the tooth, which may or may not be the height of contour of a tooth depending on the orientation of the tooth in the jaw, and extending toward the gingival line of the patient. In some instances, it can be difficult for a patient with insufficient or excessive undercut areas to secure the appliance over their teeth. For instance, an appliance placed on teeth of a patient with insufficient undercut areas may slip off the patient's teeth in an undesirable fashion and/or at undesired times; and, an appliance placed on teeth of a patient with over-sufficient undercut areas may be extremely difficult to insert causing great discomfort and/or distortion in the appliance. How well an appliance is seated on the patient's teeth can be referred to as the degree of fit of the appliance. For situations with excessive undercuts, it may be possible to fill an undercut area of a tooth with a filler material prior to the impression of the teeth and/or by blocking out the reference on the dental mold during the appliance fabrication process, so that the fit of the appliance is improved (e.g., improving the retention of the appliance onto the number of teeth). For insufficient undercuts, artificial undercuts may be created by trimming away parts of the reference model and/or by physically creating undercuts on the teeth. In any case, what is typically assumed is a single path of insertion (e.g., line of draw and/or axis of placement) and removal for a single appliance. In the event of a rigid appliance, only a single path of insertion can exist. However, for semi-rigid flexible appliances, multiple paths of insertion and removal can exist, or at least difference paths of insertion and removal for different portions of the appliance.

BRIEF DESCRIPTION OF THE DRAWINGS

FIG. 5A illustrates an example of a method for filling excessive undercut areas on a dental mold according to one or more embodiments of the present disclosure.

FIG. 5B illustrates an example of a method for filling insufficient undercut areas on a dental mold according to one or more embodiments of the present disclosure

DETAILED DESCRIPTION

Figure 1A:
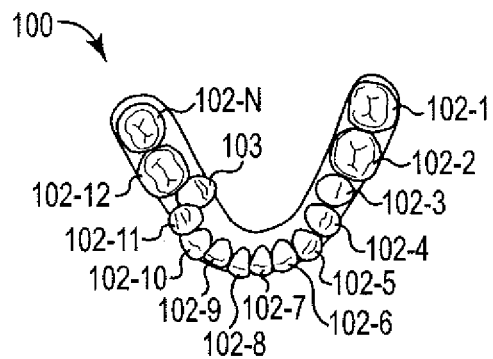
FIG. 1A illustrates an example of a digital dental model according to one or more embodiments of the present disclosure.

Dental professionals typically create a treatment plan for a patient's teeth based upon their experience with certain features and/or characteristics of dental appliances in connection with the teeth in consideration for treatment. In an ideal situation, the appliance characteristics are compatible with the condition of the teeth under consideration for treatment. For example, a dental appliance to be placed over a patient's teeth can be considered as part of a dental treatment plan. How well the dental appliance may fit over the particular patient's teeth can be a consideration, which can include the severity of undercuts and also the absence of important retention elements needed for the planned appliance to stay in place.

Typically an undercut is the portion of the appliance which engages the teeth and resists removal of the appliance in the direction of the axis of placement (e.g., path of insertion and/or removal). Resistance to placement occurs when the portion of the appliance which engages the undercut needs to first overcome the height of contour perpendicular to the axis of placement of the appliance during the insertion process. If an appliance portion is narrow because of a large undercut, the narrowness will need to stretch first in order to overcome the height of contour, thus making placement more difficult than if the undercut is less severe and the appliance is less narrow as a result. Undercuts for retaining a dental appliance therefore need to be sufficient to retain the appliance on the teeth, but not excessive so as to prevent adequate insertion or removal of the appliance.

Reducing undercut areas of teeth relative to an axis of placement of the dental appliance can be beneficial, for example, in that the reduced undercut areas can assist the patient in placing the dental appliance over the patient's teeth. This can be accomplished by filling in undercut areas of the actual teeth using block-out compounds (e.g., a light-cured resin) prior to taking an impression or scan of the patient's teeth. Or, a model of the patient's teeth can have the undercuts blocked out either physically (e.g., with block-out compound) or digitally before any appliances are made from the patient's model.

The result of reducing excessive undercuts relative to an axis of placement can be an improved ease to fitting the dental appliance on the teeth while reducing stress on the dental appliance itself when trying to place the dental appliance over the teeth of a patient. Excessive force is undesirable when placing or removing a dental appliance because the appliance may become permanently distorted or the patient may experience pain during the insertion/removal of the appliance.

An undercut area of a tooth relative to an axis of placement of a dental appliance, as used herein, can include an area between a height of contour of the tooth relative to an axis of placement and the gingiva surrounding of the tooth. Reduced stress on the semi-rigid dental appliance can result in less breakage and/or tears of the dental appliance during its use and/or during its manufacture when the appliance is being inserted and removed from the reference model of the teeth. Furthermore, a dental appliance may be more comfortable for a patient when undercut engagement areas are optimized based on information regarding the axis of placement of the dental appliance. The goal is to create an appliance which is neither too loose nor too difficult to place and remove, and to take advantage of the semi-rigid properties of the appliance in order to allow multiple axis of placement to be considered based on how the appliance flexes during insertion and removal from the teeth.

The present disclosure provides a computing device-implemented method, computing device readable medium, and mold related embodiments for filling undercut areas of teeth. For example, one or more embodiments include a non-transitory computing device medium having executable instructions that can be executed by a processor to cause a computing device to perform a method, comprising calculating an undercut area of a tooth relative to an axis of placement of a part of a dental appliance over a number of teeth and a height of contour that is defined based on the axis of placement, and filing in a part of the undercut area with a virtual filler wherein the undercut is filled to within a threshold distance from the tooth that is defined relative to the axis of placement and the height of contour. An artificial undercut may also be created and/or introduced in situations where an insufficient undercut area is present, accomplished by introducing a virtual object with at least one dimension which increases until a threshold distance is present to ensure adequate device retention.

In the following detailed description of the present disclosure, reference is made to the accompanying drawings that form a part hereof, and in which is shown by way of illustration how a number of embodiments of the disclosure may be practiced. These embodiments are described in sufficient detail to enable those of ordinary skill in the art to practice a number of embodiments of this disclosure, and it is to be understood that other embodiments may be utilized and that changes may be made without departing from the scope of the present disclosure.

As will be appreciated, elements shown in the various embodiments herein can be added, exchanged, and/or eliminated so as to provide a number of additional embodiments of the present disclosure. In addition, as will be appreciated, the proportion and the relative scale of the elements provided in the figures are intended to illustrate the embodiments of the present disclosure, and should not be taken in a limiting sense. As used herein, "a", "at least one", and "a number of" something can refer to one or more such things. Also as used herein, the designator "N", particularly with respect to reference numerals in the drawings, indicates that a number of a particular features so designated can be included.

The figures herein follow a numbering convention in which the first digit or digits correspond to the drawing figure number and the remaining digits identify an element or component in the drawing. Similar elements or components between different figures may be identified by the use of similar digits. For example, 106 may reference element "6" in FIG. 1B, and a similar element may be referenced as 206 in FIG. 2C. As will be appreciated, elements shown in the various embodiments herein can be added, exchanged, and/or eliminated so as to provide a number of additional embodiments of the present disclosure. In addition, as will be appreciated, the proportion and the relative scale of the elements provided in the figures are intended to illustrate certain embodiments of the present disclosure, and should not be taken in a limiting sense.

Although the overarching term "orthodontics" is used herein, the present disclosure is not so limited to treatments of an orthodontic nature. The present disclosure may, for instance, relate to non-orthodontic dental treatment appliances. Dental treatment appliances and/or dental appliances, as used herein, can include an appliance that is to be removeably attached to teeth. For example, dental appliances can include orthodontic appliances, surgical splints, bruxism appliances, TMJ treatment appliances, snap-on cosmetic dental appliances, removable prosthetics, and/or sleep apnea appliances, among many other removable dental appliances.

As an example, in cases of a flexible removable prosthetic (e.g., partial denture), unlike rigid prosthetics which are designed for a single axis of placement (e.g., path of insertion and/or removal), more than one axes of placement may be available for a flexible prosthetic depending on the portion of the prosthetic being inserted and the sequence of the insertion. The present disclosure may be applied to ensure that the insertion and/or removal of a flexible removable prosthetic is optimized for better retention and removal than what a single axes of placement can afford.

Digital dental models from a scan of a patient's dentition can be provided with computer-aided design and/or manufacturing systems, including tooth-treatment systems. A digital dental model representing an initial tooth arrangement may be obtained in a variety of ways.

For example, the patient's teeth may be imaged to obtain digital data using direct and/or indirect structured light, X-rays (e.g. two-dimensional and three-dimensional X-rays), lasers, destructive scanning, computer-aided tomographic images or data sets, magnetic resonance images, intra-oral scanning technology, photographic reconstruction, and/or other imaging techniques. The digital dental model can include an entire mouth tooth arrangement, some, but not all teeth in the mouth, and/or it can include a single tooth.

A physical positive model and/or negative impression of the patient's teeth or a tooth may be scanned using an X-ray, X-ray imager, laser scanner, destructive scanner, structured light, and/or other range acquisition system to produce the initial digital dental model. The data set produced by the range acquisition system may be converted to other formats to be compatible with the software (e.g., executable instructions) which is used for manipulating images within the data set, as described herein.

Referring now to FIG. 1A, there is illustrated an example of a digital dental model according to one or more embodiments of the present disclosure. As described herein, a digital dental model 100 can be obtained prior to treatment or at an intermediate stage of treatment (e.g., before treatment has completed). The digital dental model 100 can include an initial position of a number of teeth 102-1, 102-2, 102-3, 102-4, 102-5, 102-6, 102-7, 102-8, 102-9, 102-10, 102-11, 102-12 . . . 102-N, 103. For instance the number of teeth 102-1, . . . , 102-N, 103 can include a lingually displaced premolar and/or molar 103.

The digital dental model 100, as illustrated in FIG. 1A, can include a top-down view of a number of teeth 102-1, . . . , 102-N, 103. However, digital dental model embodiments of the present disclosure are not so limited to a top-down view. A digital dental model 100 can be viewed in a number of ways (e.g., side view, front view, three-dimensional view).

The digital dental model 100 in accordance with one or more embodiments can include a digital dental model of a number of teeth 102-1, . . . , 102-N, 103 located on a lower jaw of a patient, upper jaw of a patient, and/or both. The number of teeth 102-1, . . . , 102-N, 103 in the digital dental model 100 can include a tooth and/or a number of teeth with an undercut area relative to an axis of placement of a part of a dental appliance over the number of teeth and a relative height of contour that is defined based on the axis of placement.

Figure 1B:
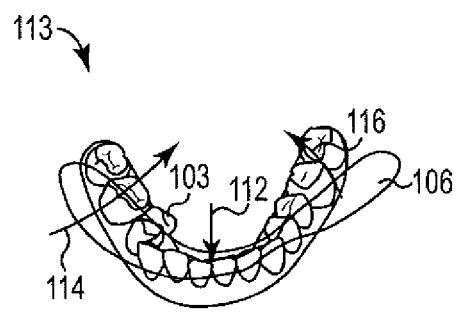
FIG. 1B illustrates an example of multiple axes of placement of parts of a dental appliance according to one or more embodiments of the present disclosure.

FIG. 1B illustrates an example 113 of multiple axes of placement 112, 114, 116 of parts of a dental appliance 106 according to one or more embodiments of the present disclosure.

Appliances can include any positioners, retainers, and/or other removable dental appliances for finishing and maintaining teeth positioning in connection with a dental treatment. These appliances may be utilized by the treatment professional in performing a treatment plan. For example, a treatment plan can include the use of a set of appliances, created according to models described herein. Appliances, in some embodiments, can include flexible dental appliances which serve in part as a prosthesis for esthetics and/or dental function.

An appliance (e.g., dental appliance 106 in FIG. 1B) can, for example, be fabricated from a polymeric shell, and/or formed from other material, having a cavity shaped to receive and apply force to reposition one or more teeth from one teeth arrangement to a successive teeth arrangement. The shell may be designed to fit over a number of, or in many instances all, teeth present in the upper and/or lower jaw.

A dental appliance is often positioned on a number of teeth in multiple steps where a first part of the dental appliance is placed over a first set of teeth and a second part is subsequently places over a second set of teeth. In such embodiments, the placement of each part may have a different axis of placement. When the appliance is removed, the removal of each part may have a different axis of removal. The removal axis and/or axes, in some embodiments, may not be the same as the placement axis and/or axes. Nor does removal need to be in the same sequence as the placement.

The embodiment of FIG. 1B illustrates multiple axes of placement 112, 114, 116 of a dental appliance 106 and can include a defined estimated path of placement of a part of the dental appliance 106 over a number of teeth. A vector representing the path of placement of a part of the dental appliance can include a line of draw of the dental appliance.

For instance, as discussed above, a dental appliance can have multiple axes of placement. Multiple axes of placement can include axes of placement 112, 114, 116 of different parts of the dental appliance 106 over the number of teeth. An axis of placement 112, 114, 116 can include any direction of travel of an appliance as it is to be placed over one or more teeth. A part of the dental appliance 106 can include an anterior region, a posterior right region, and/or a posterior left region, for example. In examples of the present disclosure, an axis of placement can include a buccal to lingual path and/or a lingual to buccal path, among other paths.

In the some embodiments of the present disclosure, as illustrated in FIG. 1B, multiple axes of placement 112, 114, 116 can include two axes of placement of parts of a dental appliance 106 over a number of teeth can include a first axis of placement 112 of a first part of a dental appliance 106 and a second axis of placement 114, 116 of a second part of a dental appliance 106. For example, the first part of the dental appliance 106 can be placed over a number of teeth (e.g., a first sub-number of teeth among the number of teeth) along the first axis of placement 112, and the second part of the dental appliance 106 can be placed over a number of teeth (e.g., a second sub-number of teeth among the number teeth) along the second axis of placement 114, 116, and/or any combination thereof. A sum of the first sub-number of teeth and the second sub-number of teeth can include the number of teeth (e.g., a total number of teeth of the patient that the dental appliance is to be placed on), for instance.

The first axis of placement 112 can, for example, be with respect to an anterior path. As used herein, an anterior path can include placement of an anterior part of the dental appliance 106 over one or more of a patient's incisor teeth and/or canine teeth. A second path 114, 116 can include a posterior path. As used herein, a posterior path can include placement of a posterior part of the dental appliance 106 over one or more of a patient's premolar teeth and molar teeth. For instance, a posterior path can include a posterior right path and/or a posterior left path. Thereby, an anterior part of a dental appliance 106 can be placed over the anterior teeth of a patient along a first axis of placement 112 and then a posterior part of the dental appliance 106 (e.g., posterior right part and/or posterior left part of the dental appliance) can be placed over the posterior teeth of the patient along a second axis of placement 114, 116.

In accordance with some embodiments of the present disclosure, multiple axes of placement 112, 114, 116 can include three axes of placement 112, 114, 116, as illustrated in FIG. 1B. Three axes of placement can include a first axis of placement 112 of a first part of a dental appliance 106, a second axis of placement 114 of a second part of the dental appliance 106, and a third axis of placement 116 of a third part of the dental appliance 106. For example, the first part of the dental appliance 106 can be placed over a number of teeth (e.g., a first sub-number of teeth among the number of teeth) along the first axis of placement 112, the second part of the dental appliance 106 can be placed over a number of teeth (e.g., a second sub-number of teeth among the number of teeth) along the second axis of placement 114, the third part of the dental appliance 106 can be placed over a number of teeth (e.g., a third sub-number of teeth) along the third axis of placement 116, and/or any combination thereof. A sum of the first sub-number of teeth, the second sub-number of teeth, and the third sub-number of teeth can include the number of teeth, for instance.

The first axis of placement 112 can include an anterior path, the second axis of placement 114 can include a posterior left path, and the third axis of placement 116 can include a posterior right path, for example. Each axis of placement 112, 114, 116 can include a diagonal, a vertical, and/or a horizontal path in one or more dimensions from a buccal to lingual side of the sub-number of teeth and/or lingual to buccal side of the sub-number of teeth, for example. Thereby, an anterior part of a dental appliance 106 can be placed over the anterior teeth of a patient along a first axis of placement 112, then a posterior left part of the dental appliance 106 can be placed over the posterior left teeth of the patient along a second axis of placement 114, and then a posterior right part of the dental appliance 106 can be placed over the posterior right teeth of the patient along a third axis of placement 116.

Although a patient may generally follow an anterior path followed by a posterior path (e.g., posterior right followed by posterior left and/or posterior left followed by posterior right) to place a dental appliance 106 over a number of teeth, paths of placement of the dental appliance 106 of the present disclosure are not so limited and can include additional paths.

For example, in one or more embodiments of the present disclosure, the placement of the dental appliance 106 over the number of teeth can follow an alternative pattern. For instance, an anterior part of a dental appliance 106 can be placed over the anterior teeth of the patient along the first axis of placement 112, then a posterior right part of the dental appliance 106 can be placed over the posterior right teeth of the patient along the third axis of placement 116, and then a posterior left part of the dental appliance 106 can be placed over the posterior left teeth of the patient along the second axis of placement 114. In addition, the placement of the dental appliance 106 can include a posterior left path, followed by a posterior right path, and then followed by an anterior path, and/or a posterior right path, followed by a posterior left path, and then followed by an anterior path. Alternatively, the placement of the dental appliance 106 can include a posterior left path, followed by an anterior path, and then followed by a posterior right path, and/or a posterior right path, followed by an anterior path, and then followed by a posterior left path, for example.

A number of axes of placement 112, 114, 116 and/or a non-vertical axis of placement in one or more dimensions in accordance with various embodiments of the present disclosure can be used to place a dental appliance 106 over a number of teeth, wherein the number of teeth include multiple undercut areas of the teeth relative to an axis of placement of different parts of the dental appliance over the number of teeth. For instance, a patient with a number of retroclined incisors and/or a number of blocked out bicuspids 103 may have an easier time inserting a dental appliance over the patient's teeth by using multiple axes of placement 112, 114, 116 compared to using a single axis of placement. A retroclined incisor can include a retroclined lower and/or upper incisor, for example. A blocked out bicuspid 103 can, for instance, include a lingually displaced upper and/or lower premolar and/or molar.

When the appliance 106 is placed over the anterior teeth of FIG. 1B, the appliance may expand and/or widen if the configuration of the teeth receptacles in the appliance is different than the actual configuration of the teeth (as is needed in the case of sequential positioning appliances). This can make the path the other parts of the appliance must take in order to seat different than the path of the appliance in the otherwise unwidened state. A tooth which is excessively displaced, such as tooth 103, becomes particularly challenging to seat the appliance over, if a large discrepancy exists between the path needed and the path available as a result of the transient appliance expansion when the appliance is first seated in the front teeth. Arrows 114 and 116 represent the additional displacement of the appliance which is needed in order to align the respective parts of the appliance on the teeth in a way that minimizes the resistance from the undercuts present.

As illustrated in FIG. 1B, some embodiments of the present disclosure can include an axis of placement calculated and/or estimated in light of potential flexion of the appliance 106 during seating and/or removal of the initial portion (e.g., first axis of placement 112). The one or more axes of placement for each part of the appliance 106 can include an arch and/or with the flexion built in. The flexion can be, for example, built in and/or presumed in the appliance and the multiple axes of placement can account for appliance flexion. For example, calculating the axes of placements can include factoring for dental appliance flexion when placed over the number of teeth based on a material property of the dental appliance. Alternatively, in various embodiments, an appliance may not have any flexion but may still have multiple axes of placement and/or removal.

An axis of placement of part of a dental appliance can be determined, for example, by observations of a patient and/or observations of similar patients. A similar patient, for instance, can include a patient with a similar and/or identical number of teeth and/or digital dental model. As an example, a similar patient to a patient with a lingually displaced lower right premolar 103 can include a person with a lingually displaced lower right premolar and/or molar.

In a number of embodiments, an axis of placement can be calculated and/or determined based upon data of previous placements of dental appliances, such as observations of a patient, in combination with a method comprising calculating an undercut area of a tooth relative to an axis of placement of a part of a dental appliance over a number of teeth and a height of contour that is defined based on the axis of placement and filling in a part of the undercut area with a virtual filler wherein the undercut is filled to within a threshold distance from the tooth that is defined relative to the axis of placement and the height of contour.

The sequence of placement of the appliance (e.g., pattern of axes of placement and/or path of draw), in some embodiments of the present disclosure, can alter one or more axes of placement of parts of the appliance 106. For instance, a first axis of placement for a first part of a dental appliance 106 may affect a second axis of placement for a second part of the dental appliance 106. In addition, the removal sequence of the dental appliance 106 may not be the same as the placement sequence.

Figure 2A:
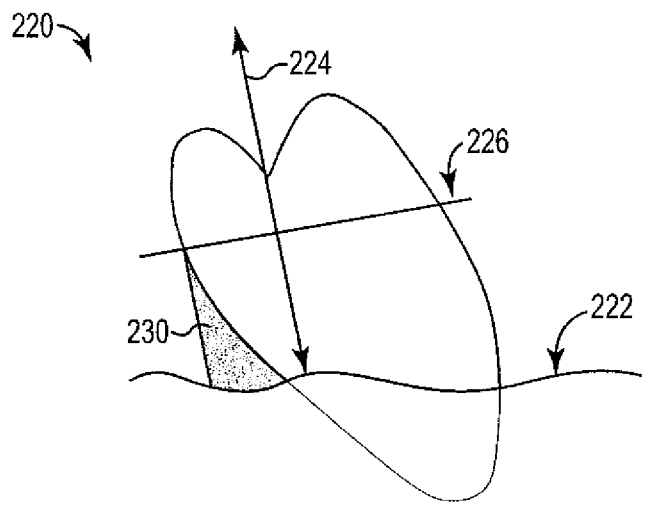
FIG. 2A illustrates an example of a height of contour and an undercut area of a tooth that is defined based on an estimated axis of placement of part of a dental appliance according to one or more embodiments of the present disclosure.
Figure 2B:
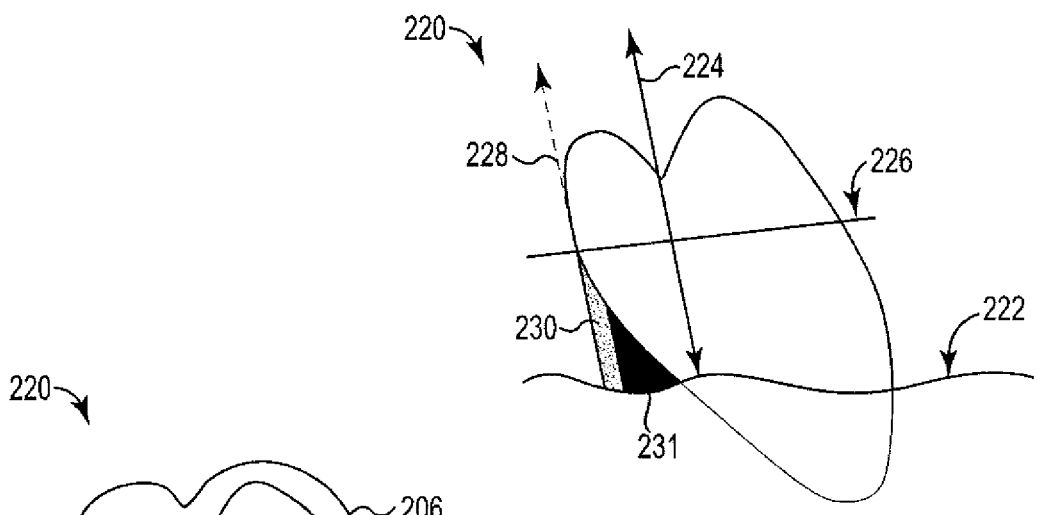
FIG. 2B illustrates an example of a virtual filler filled in part of an undercut area of a tooth according to one or more embodiments of the present disclosure.

FIG. 2A illustrates an example of a relative height of contour 226 and an undercut area of a tooth 220 that is defined based on an estimated axis of placement 224 of a part of a dental appliance according to one or more embodiments of the present disclosure. The relative height of contour 226 of the tooth 220, as illustrated in the embodiment of FIG. 2A, can be relative to an axis of placement 224 of the part of the dental appliance. A relative height of contour 226 may not necessary be the anatomically fattest part of a tooth relative to the tooth's long axis. The tooth 220, as illustrated in the embodiment of FIGS. 2A and 2B, can include a tooth 220 with an excessive undercut area.

In contrast, an anatomical height of contour can include a line encircling a tooth 220 representing the greatest circumference of the tooth. The height of contour of the tooth, for instance, can encircle the tooth in a generally horizontal manner. An undercut area of a tooth 220 can include an area between the height of contour of the tooth 220 and a gingiva of the tooth 222. An anatomical height of contour can presume the tooth to be in an ideal aligned position (e.g., final position).

As used herein, however, a relative height of contour 226 of a tooth 220 can be defined based on an axis of placement 224 of part of a dental appliance. A height of contour 226 of a tooth 200 defined based on an axis of placement 224 of part of a dental appliance can, for example, include a line encircling a tooth representing the greatest circumference of the tooth relative to and/or with respect to an axis of placement 224 of part of a dental appliance. For instance, a greatest circumference of a tooth 220 can include a greatest radius, bulge, convexity, and/or diameter of a tooth 220.

When the axis of placement of at least a portion of the appliance changes (e.g., because of temporary appliance flexure during partial placement), the relative height of contour to the unseated portions can also change. In some instances, the change can be unfavorable, such that the placement of the unseated portions of the appliance can become difficult and/or impossible without first significantly altering the appliance and/or causing discomfort to the patient.

In accordance with one or more embodiments of the present disclosure, an undercut area of a tooth relative to an axis of placement can be calculated. For example, in the embodiment of FIG. 2A, the undercut area 230 of a tooth 220 relative to an axis of placement 224 can include an area between the height of contour 226 of the tooth 220 relative to an axis of placement 224 and the gingiva of the tooth 222 (e.g., gum line 222 of the tooth 220).

FIG. 2B illustrates an example of a virtual filler 231 filled in part of an undercut area 230 of a digital tooth 220 according to one or more embodiments of the present disclosure. The virtual filler 231 acts to reduce the undercut area relative to at least one axis of placement for the appliance, so that when an appliance is made over a model with the fillers physically in place, the appliance becomes easier to place and remove along at least one axis of placement. For instance, an undercut area 230 of a tooth 220 and/or multiple undercut areas of a number of teeth relative to an axis of placement 224 can be filled with virtual filler 231 on a digital dental model of the tooth 220 and/or the number of teeth. A virtual filler 231 can include a two-dimensional (2D) virtual representation, three-dimensional (3D) virtual representation, and/or other representations of a filler material. A physical filler material can be any additional material that can be added to a physical dental mold of a patient's tooth and/or teeth to fill a space (e.g., which can include prosthetic teeth such as pontics). The additional material can include the same and/or different material than the physical dental mold of the patient's teeth. For example, the filler can be integrated as part of the dental model when the model is milled or fabricated using stereolithography processes. Or the filler may be a different material from the dental model, such as a silicone putty corresponding to the 3D shapes of the virtual filler 231.

In some examples of the present disclosure, the undercut area 230 of a virtual tooth 220 can be filled with a virtual filler 231 to a threshold distance from the tooth 220 that is defined relative to the axis of placement 224 and the relative height of contour 226. For instance, the threshold distance from the tooth can be defined by a line parallel 228 to the axis of placement 224 and tangential to the height of contour 226. A threshold distance from the tooth 220, for instance, can include a numerical value (e.g., 0.50 millimeters) representing a distance from the tooth 220 and/or line parallel 228 to the axes of placement 224 (e.g., the line of draw for an appliance). For example, a part of the undercut area 231 of the tooth 220 can be filled in response to identifying that a part of the calculated undercut area 230 of the tooth 220 is not within the threshold distance. For instance, a part of the calculated undercut 230 area may not be within a threshold distance from the tooth 220 in response to the undercut area 230 being outside (e.g., less than, greater than) the threshold distance from the line parallel 228 to the axis of placement 224 and tangential to the height of contour 226.

Figure 2C:
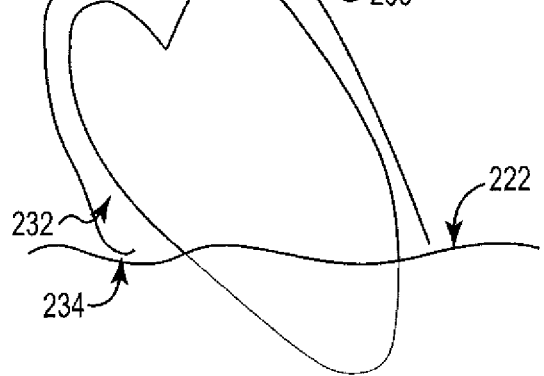
FIG. 2C illustrates an example of a dental appliance according to one or more embodiments of the present disclosure.

FIG. 2C illustrates an example of a dental appliance 206 according to one or more embodiments of the present disclosure. The dental appliance 206 can include an area 232 created based on use of a virtual filler (e.g., virtual filler 231 from FIG. 2B) on a digital dental model and/or from physical filler material added to a physical dental mold.

The dental appliance 206 can be made, for example, by thermal-forming a piece of plastic over a physical dental mold. The physical dental mold, for instance, can represent an incremental position to which a patient's teeth are to be moved. The physical dental mold can be manufactured by downloading a Computer-aided Design (CAD) digital dental model to a rapid prototyping process, such as, for example, a Computer-aided manufacturing (CAM) milling, stereolithography, and/or photolithography. The digital dental mold can be hollowed out or "shelled" before sent for manufacturing save on material cost, for example.

In some embodiments of the present disclosure, the dental mold can include a virtual and/or physical filler material added to an undercut area of a molded tooth relative to an axis of placement of the dental appliance 206 over the number of teeth. The filler material, for instance, can be located to within a threshold distance of the molded tooth.

A dental appliance 206 can be formed by layering a thermoformable sheet of material and/or multiple sheets of one or more materials over the dental mold. The materials can include a polymeric material, for instance. Generally, the dental appliance 206 is produced and/or formed by heating the polymeric thermoformable sheet and vacuum or pressure forming the sheet over the dental mold (e.g., number of molded teeth). The shape of the sheet of material can change thickness on some portions of the sheet as it conforms to the mold shape. A dental appliance 206 can, for example, include a negative impression of the dental mold. The appliance and/or parts thereof may be transparent, semitransparent, or opaque in such a way as to emulate a nature tooth shade.

For instance, a dental appliance 206 formed using a dental mold including a filler material located in an undercut area of a molded tooth relative to an axis of placement of the dental appliance 206 can include a filler space 232 between the dental appliance 206 and the tooth 220. The filler space can be created by a filler material on the dental mold. The filler material can be virtually attached to the digital dental model and created at the same time as the dental mold (e.g., virtual filler material), and/or can be added to the physical dental mold after the physical dental mold is formed (e.g., physical filler material). The filler space 232 created can include a hollow space on an inner side of the dental appliance 206. For instance, an inner side of the dental appliance 206 can include a hollow space proximal to the lingual surface of a tooth 220 and/or proximal to a buccal surface of a tooth 220.

In some embodiments of the present disclosure, a dental appliance 206 can include a smooth edge 234 of the dental appliance 206 proximal to a gingival line of a patient 222. For instance, the smooth edge 234 can be created by creating a smooth inward-directed (e.g., towards the tooth/gums) transition on a virtual and/or physical dental mold from the filler material to the molded tooth and/or number of molded teeth. The smooth edge 234 can reduce or prevent discomfort to a patient's tissue (e.g., tongue, lips, and gum), for example.

Figure 3:
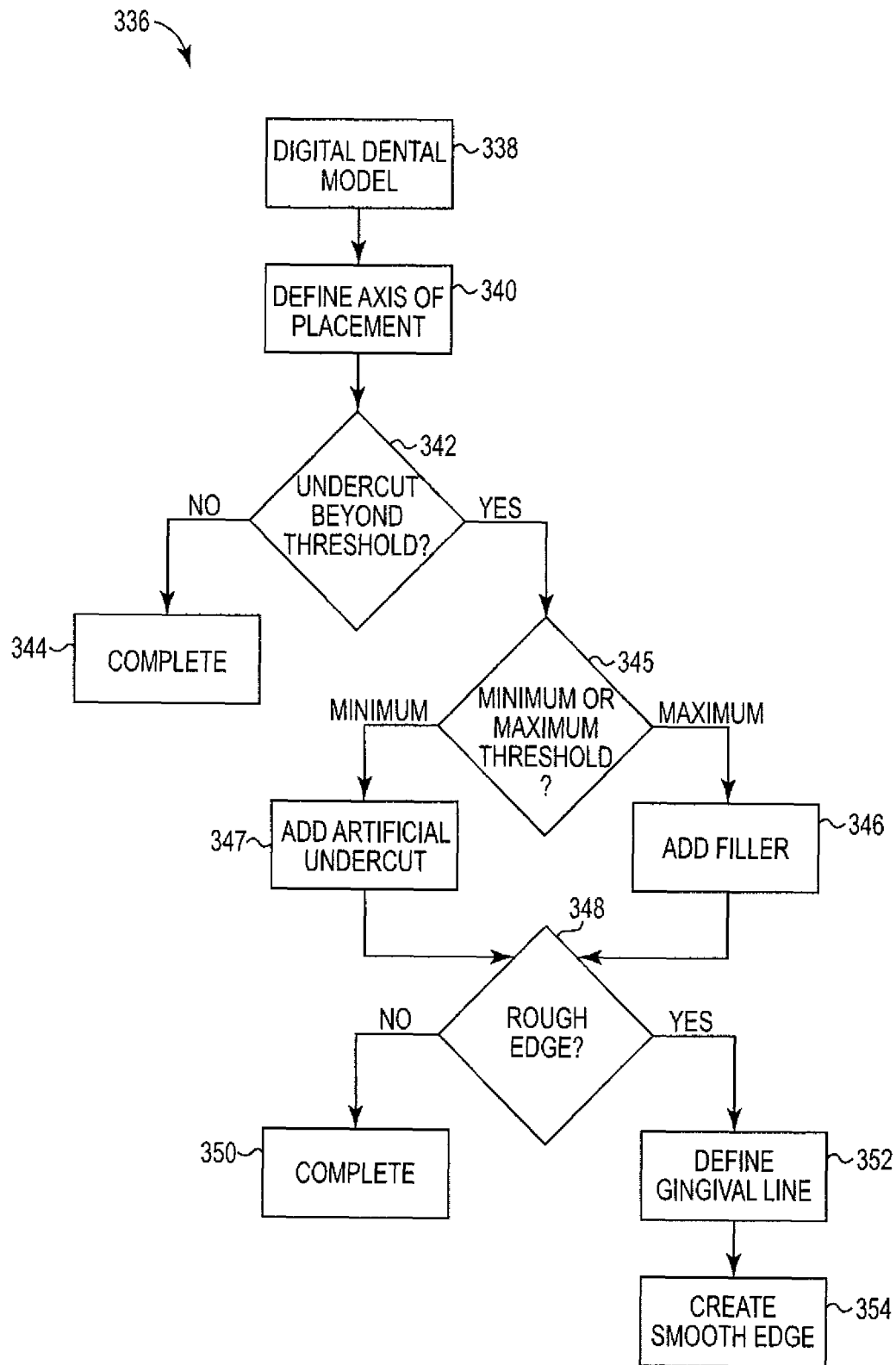
FIG. 3 is a flow diagram illustrating an example of a method for filling undercut areas according to one or more embodiments of the present disclosure.

FIG. 3 is a flow diagram illustrating an example of a method for filling undercut areas according to one or more embodiments of the present disclosure. At 338, the method 336 can include creating and/or receiving a digital dental model. For example, a digital dental model can be created from a scan of a patient's dentition and provided with computer-aided design and/or manufacturing systems, including tooth-treatment systems. The digital dental model can include data for a number of teeth. The digital dental model can include an initial digital dental model or an intermediate position digital dental model, for example.

At 340, the method 336 can include defining and/or determining an axis of placement of a part of a dental appliance. For example, the axis of placement can be calculated, determined, and/or identified from observations of a patient and/or one or more similar patients. In various embodiments of the present disclosure, axes of placement of different parts of the dental appliance can be defined.

At 342, the method 336 can include determining whether an undercut area of a tooth that is not within a threshold distance of the tooth exists. The determination can include calculating an undercut area of a tooth and/or multiple undercut areas of a number of teeth relative to an axis of placement of a part of a dental appliance and/or axes of placement of different parts of the dental appliance over the number of teeth. An undercut area of a tooth beyond a threshold distance can include a part of a calculated undercut area of a tooth that is not within a threshold distance from a line parallel to the axis of placement and tangential to the height of contour.

A threshold distance from a line parallel to the axis of placement and tangential to the relative height of contour can include a maximum distance and/or a minimum distance from the line parallel to the axis of placement and tangential to the relative height of contour. For example, an undercut area of a tooth that is over a maximum threshold area can be determined. This can represent an area of an appliance that may be excessively retentive relative to a particular axis of placement. A maximum threshold area can include an undercut area of a tooth and/or part of an undercut area of the tooth that is greater than a threshold distance from the line (e.g., a maximum threshold distance)

Alternatively and/or in addition, an undercut area of a tooth that is not at least a minimum threshold area may be determined. This can represent an area of an appliance which may be insufficiently retentive relative to a particular axis of placement. A minimum threshold area can include an undercut area of a tooth and/or part of a tooth that is less than a threshold distance from the line parallel to the axis of placement and tangential to the relative height of contour (e.g., minimum threshold distance). In such a situation, the insufficient undercut may be supplemented by the addition of an artificial undercut such as dental protrusions attached to the surfaces of the teeth.

In a number of embodiments, identifying that a part of the calculated undercut area of the tooth is not within the threshold distance (e.g., above and/or below) can be included in any one of, or any combination of: a method comprising calculating an undercut area of a tooth relative to an axis of placement of a part of a dental appliance over a number of teeth and a relative height of contour that is defined based on the axis of placement (e.g., line of draw) and filling in a part of the undercut area with a virtual filler wherein the undercut area is filled to within a threshold distance from the tooth that is defined relative to the axis of placement of a part of the dental appliance over the number of teeth and a relative height of contour and/or supplementing an insufficient undercut area with an artificial undercut; the method, wherein the axis of placement of the dental appliance defines an estimated path of placement of the part of the dental appliance over the number of teeth; the method, wherein calculating the undercut area of the tooth further includes filling in the part of the undercut area with a virtual filler wherein the undercut is filled and/or an artificial undercut is introduced to within a threshold distance from the tooth that is defined by a line parallel to the axis of placement and tangential to the relative height of contour; and, the method, including calculating multiple undercut areas of the number of teeth relative to axes of placement of different parts of the dental appliance over the number of teeth.

In response to determining that no undercut area exists, the method 336 can be complete 344. In response to determining that an undercut area beyond a threshold exists, the method 336 can include determining whether the undercut area is beyond a minimum threshold and/or a maximum threshold 345. Determining can include identifying if an undercut area of the tooth is greater or less than a threshold distance from the line, for instance. An undercut area greater than a threshold distance (e.g., maximum threshold area and/or distance) can include an excessive undercut area. An undercut area less than a threshold distance (e.g., minimum threshold area and/or distance) can include an insufficient undercut area.

In response to determining that an excessive undercut area exists (e.g., greater than a maximum threshold), the method 336 can include adding virtual filler to the undercut area of a tooth 346. Adding virtual filler can, for example, include filling in a part of the undercut area and/or part of each of the multiple undercut areas with virtual filler wherein the undercut area of the tooth and/or each tooth is filled to within a threshold distance that is defined relative to the one or more axes of placement and the height of contour nearest the tooth and/or each tooth. For example, adding virtual filler can include adding a representation of a filler material to an undercut area of a tooth to within a threshold distance from the tooth that is defined by a line parallel to the axis of placement and tangential to the height of contour. In various embodiments of the present disclosure, an alternative response can include determining that artificial undercuts that are planned as part of the treatment plan for specific tooth movements (e.g., rotation, inclination, and/or angulation) may be altered to reduce the amount of undercut relative to the height of contour relative to the axis of placement.

In response to determining that an insufficient undercut area exists (e.g, less than a minimum threshold), the method 336 can include adding and/or creating an artificial undercut to the undercut area of a tooth 347. An artificial undercut are can include a pressure point and/or an attachment. A pressure point, as used herein, can include virtual and/or physical removal of certain areas of the reference model. An attachment, as used herein, can include a protruding apparatus that can be added (e.g., as further discussed in FIG. 6B).

In various embodiments of the present disclosure, one or more excessive undercut areas and one or more insufficient undercut areas can exist. For example, the one or more excessive undercut areas and the one or more insufficient undercut areas can be identified and/or located on the same tooth and/or separate teeth.

In some embodiments of the present disclosure, the method 336 can include determining if a rough edge exists on the digital dental model 348. For instance, a rough edge can include an edge of the dental appliance proximal to a gingival line of a patient that is not convex relative to a tooth and/or tissue of a patient (e.g., inward facing towards the teeth/gums) and/or not within a threshold distance of the gingival line of the patient.

In response to determining no rough edges exist, the method 336 can be complete 350. In response to determining a rough edge and/or multiple rough edges exist, the method 336 can include defining an edge of the dental appliance proximal to a gingival line of a patient 352. For instance, an edge of the dental appliance proximal to the gingival line of a patient can include an edge near, touching, and/or close to the gingival line of the patient. A rough edge can be, for instance, created by the virtual filler and/or an artificial undercut, among other surfaces.

At 354, the method can include creating a smooth transition of the virtual filler and/or a gap created by the artificial undercut (e.g., as discussed further in FIG. 6B) to the defined edge. For instance, a smooth transition can include an accommodation in the dental appliance that wraps around and/or near a surface of the tooth. The surface of the tooth, for instance, can include a buccal and/or lingual surface. The smooth transition of the virtual filler and/or gap created by the artificial undercut to the defined edge, for example, can include a convex shape relative to the patient's teeth and/or tissue.

In some embodiments of the present disclosure, creating a smooth edge of the virtual filler can be included in any one of, or any combination of: a method comprising calculating an undercut area of a tooth relative to an axis of placement of a part of a dental appliance over a number of teeth and a height of contour that is defined based on the axis of placement and filling in a part of the undercut area with a virtual filler wherein the undercut area is filled to within a threshold distance from the tooth that is defined relative to the axis of placement (e.g., line of draw) of a part of the dental appliance over the number of teeth and a height of contour; the method, wherein the axis of placement of the dental appliance defines an estimated path of placement of the part of the dental appliance over the number of teeth; the method, wherein calculating the undercut area of the tooth further includes filling in the part of the undercut area with a virtual filler wherein the undercut is filled to within a threshold distance from the tooth that is defined by a line parallel to the axis of placement and tangential to the height of contour; and, the method, including calculating multiple undercut areas of the number of teeth relative to axes of placement of different parts of the dental appliance over the number of teeth. In the event of insufficient undercut according to a minimum threshold, an artificial undercut can be added either manually or automatically, through the addition of artificial undercuts such as protrusions to be bonded into place onto the teeth by the practitioner and/or virtual removal of material from the appliance.

As an example, creating a smooth edge of virtual filler can be included in a method comprising calculating one or more axes of placement of a dental appliance over a number of teeth based upon data of previous placements of dental appliances, calculating an undercut area of a tooth relative to the one or more axis of placement of a part of the dental appliance over the number of teeth (e.g., the calculated one or more axis of placement of the dental appliance) and a height of contour that is defined based on the axis of placement, and filling in a part of the undercut area with a virtual filler wherein the undercut area is filled to within a threshold distance from the tooth that is defined relative to the axis of placement of a part of the dental appliance over the number of teeth and a height of contour.

Figure 4:
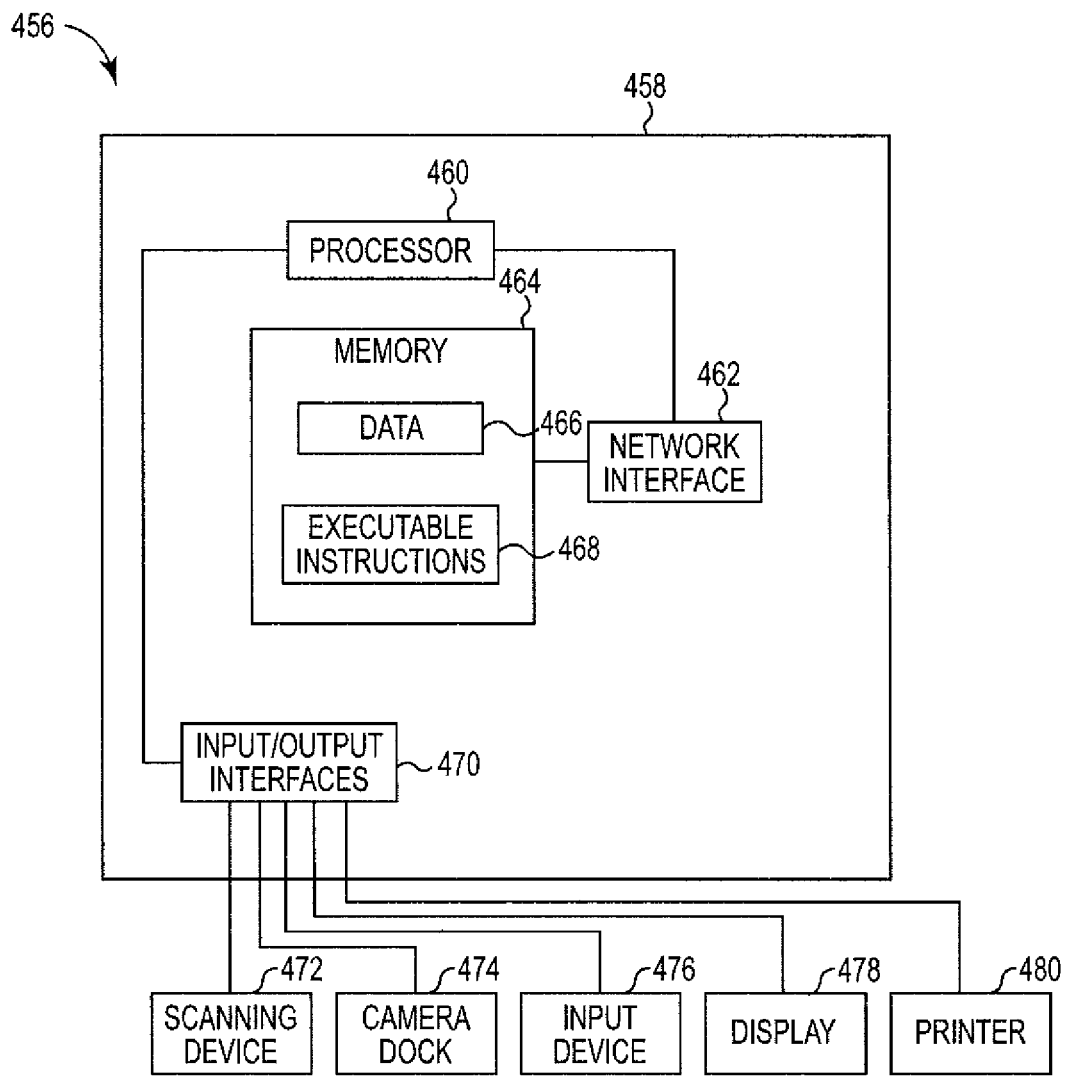
FIG. 4 illustrates an example computing device readable medium 456 having executable instructions that can be executed by a processor to perform a method according to one or more embodiments of the present disclosure.

FIG. 4 illustrates an example computing device readable medium 456 having executable instructions that can be executed by a processor to perform a method according to one or more embodiments of the present disclosure. For instance, a computing device 458 can have a number of components coupled thereto. The computing device 458 can include a processor 460 and a memory 464. The memory 464 can have various types of information including data 466 and executable instructions 468, as discussed herein.

The processor 460 can execute instructions 468 that are stored on an internal or external non-transitory computer device readable medium (CRM). A non-transitory CRM, as used herein, can include volatile and/or non-volatile memory. Volatile memory can include memory that depends upon power to store information, such as various types of dynamic random access memory (DRAM), among others. Non-volatile memory can include memory that does not depend upon power to store information.

Memory 464 and/or the processor 460 may be located on the computing device 458 or off the computing device 458, in some embodiments. As such, as illustrated in the embodiment of FIG. 4, the computing device 458 can include a network interface 462. Such an interface 462 can allow for processing on another networked computing device, can be used to obtain information about the patient, and/or can be used to obtain data and/or executable instructions for use with various embodiments provided herein.

As illustrated in the embodiment of FIG. 4, the computing device 458 can include one or more input and/or output interfaces 470. Such interfaces 470 can be used to connect the computing device 458 with one or more input and/or output devices 472, 474, 476, 478, 480.

For example, in the embodiment illustrated in FIG. 4, the input and/or output devices can include a scanning device 472, a camera dock 474, an input device 476 (e.g., a mouse, a keyboard, etc.), a display device 478 (e.g., a monitor), a printer 480, and/or one or more other input devices. The input/output interfaces 470 can receive executable instructions and/or data, storable in the data storage device (e.g., memory), representing a digital dental model of a patient's dentition.

In some embodiments, the scanning device 472 can be configured to scan one or more physical dental molds of a patient's dentition. In one or more embodiments, the scanning device 472 can be configured to scan the patient's dentition and/or dental appliance directly. The scanning device 472 can be configured to input data into the computing device 458.

In some embodiments, the camera dock 474 can receive an input from an imaging device (e.g., a 2D or 3D imaging device) such as a digital camera, a printed photograph scanner, and/or other suitable imaging device. The input from the imaging device can, for example, be stored in memory 464.

The processor 460 can execute instructions to provide a visual indication of a treatment plan, an axis of placement, and/or an undercut area of a tooth relative to an axis of placement on the display 478. The computing device 458 can be configured to allow a treatment professional or other user to input treatment goals. Input received can be sent to the processor 460 as data 466 and/or can be stored in memory 464.

Such connectivity can allow for the input and/or output of data and/or instructions among other types of information. Some embodiments may be distributed among various computing devices within one or more networks, and such systems as illustrated in FIG. 4, can be beneficial in allowing for the capture, calculation, and/or analysis of information discussed herein.

The processor 460, in associated with the data storage device (e.g., memory 464), can be associated with the data 466. The processor 460, in association with the memory 464, can store and/or utilize data 466 and/or execute instructions 468 for filling undercut areas of teeth relative to axes of placement different parts of a dental appliance. Such data can include the digital dental model and/or a defined axis of placement.

The processor 460 coupled to the memory 464 can cause the computing device 458 to perform a method including, for example, calculating an undercut area of a tooth relative to an axis of placement of a part of a dental appliance over a number of teeth and a height of contour based on the axis of placement. In various embodiments of the present disclosure, the processor 460 coupled to the memory 464 can cause the computing device to perform the method including calculating multiple undercut areas of the number of teeth relative to axes of placement of different parts of the dental appliance over the number of teeth. For instance, the multiple axes of placement can include an anterior line of draw, a posterior left line of draw, a posterior right line of draw, and/or any combination thereof.

In accordance with one or more embodiments of the present disclosure, an axes of placement including an anterior line of draw, a posterior left line of draw, and a posterior right line of draw can be included in any one of, or any combination of: a method comprising calculating multiple undercut areas of a number of teeth relative to axes of placement of different parts of a dental appliance over a number of teeth and filing in a part of the undercut area with a virtual filler wherein the undercut of each tooth is filled to within a threshold distance that is defined relative to the one or more axis of placement and the relative height of contours nearest the tooth; the method, wherein calculating multiple undercut areas includes calculating undercut areas relative to a first axis of placement of a first part of the dental appliance over a number of teeth and a height of contour that is defined based on the first axis of placement, and a second axis of placement of a second part of the dental appliance over a number of teeth and a height of contour that is defined based on the second axis of placement; the method, wherein the first axis of placement corresponds to an anterior part of the dental appliance and the second axis of placement corresponds to a posterior part of the dental appliance; the method, wherein the first axis of placement corresponds to an anterior part of the dental appliance and the second axis of placement corresponds to one of a posterior left part of the dental appliance and a posterior right part of the dental appliance.

In some examples, an axes of placement including an anterior line of draw, a posterior left line of draw, and a posterior right line of draw can be included in any one of, or any combination of: a method comprising calculating multiple undercut areas of a number of teeth relative to axes of placement of different parts of a dental appliance over a number of teeth and filing in a part of the undercut area with a virtual filler wherein the undercut of each tooth is filled to within a threshold distance that is defined relative to the one or more axis of placement and the relative height of contours nearest the tooth; the method, wherein calculating multiple undercut areas includes calculating undercut areas relative to a first axis of placement of a first part of the dental appliance over a number of teeth and a height of contour that is defined based on the first axis of placement, a second axis of placement of a second part of the dental appliance over a number of teeth and a height of contour that is defined based on the second axis of placement, and a third axis of placement of a third part of the dental appliance over a number of teeth and a height of contour that is defined based on the third axis of placement; and, the method, wherein the first axis of placement corresponds to an anterior part of the dental appliance, the second axis of placement corresponds to a posterior left part of the dental appliance, and the third axis of placement corresponds to a posterior right part of the dental appliance.

The processor 460 coupled to the memory 464 can cause the computing device 458 to perform a method including filling in a part of the undercut area with a virtual filler wherein the undercut is filled to within a threshold distance from the tooth that is defined relative to the axis of placement and the height of contour.

In some embodiments of the present disclosure, the processor 460 coupled to the memory 464 can cause the computing device 458 to perform a method including calculating an axis of placement of part of the dental appliance over the number of teeth based upon data of previous placements of dental appliances. For instance, calculating an axis of placement can include defining the axis of placement using an undercut draft. An undercut draft can include minimizing a number of geometric shapes perpendicular to an axis of placement. The minimized number of geometric shapes can be compared to a threshold number of geometric shapes. A geometric shape, for instance, can include a triangle, a rectangle, and/or a quadrilateral, among many other geometric shapes.

The data of previous placements of dental appliances can include data of one or more axes of placement of dental appliances over similar patient's teeth. For instance, a similar patient can include a patient with a similar arranged number of teeth of patients and/or similar initial digital dental models. Axes of placement of dental appliances over similar patient's teeth can be used as an initial axis of placement over the patient number of teeth and the number of geometric shapes can be minimized, for instance. The data can also include inputs from a treatment professional and/or other user of observed axes of placements of the patient and/or similar patients. The input from treatment professional and/or other user can be input by the treatment professional and/or other user on the computing device 458 and/or a separate computing device. The separate computing device and the computing device 458 can communicate using the network interface 462, for instance.

In a number of embodiments of the present disclosure, calculating an axis of placement of the dental appliance over the number of teeth based upon data of previous placements of dental appliances can be included in any one of, or any combination of: a method comprising calculating an undercut area of a tooth relative to an axis of placement of a part of a dental appliance over a number of teeth and a height of contour that is defined based on the axis of placement and filling in a part of the undercut area with a virtual filler wherein the undercut area is filled to within a threshold distance from the tooth that is defined relative to the axis of placement of a part of the dental appliance over the number of teeth and a height of contour; the method, wherein the axis of placement of the dental appliance defines an estimated path of placement of the part of the dental appliance over the number of teeth; the method, wherein calculating the undercut area of the tooth further includes filling in the part of the undercut area with a virtual filler wherein the undercut is filled to within a threshold distance from the tooth that is defined by a line parallel to the axis of placement and tangential to the height of contour; and, the method, including calculating multiple undercut areas of the number of teeth relative to axes of placement of different parts of the dental appliance over the number of teeth.

FIG. 5A illustrates an example of a method for filling excessive undercut areas on a dental mold according to one or more embodiments of the present disclosure. At 584, the method 582 can include creating a set of molded teeth from a digital model of a number of teeth of a patient. A digital model, for example, can include an initial digital dental model and/or intermediate digital dental model. A dental mold can be formed in accordance with a unique treatment file that identifies a patient, a stage of a treatment plan, the digital model of the number of teeth, and/or whether the dental mold is of the upper and/or lower dental arch.

In some embodiments, a treatment file can be accessed by a rapid prototyping apparatus machine, such as a SLA or printing, to form and/or create the dental mold. The result of the dental mold can include a set of molded teeth. The set of molded teeth can include at least a replica of the number of teeth of the patient. The dental mold can be used to make a dental appliance, for example, by creating a negative impression of the dental mold using polymeric sheets of material and vacuum forming the sheets over the dental mold, as discussed above.

At 586, the method 582 can include adding a filler material to a first number of the molded teeth among the set of molded teeth, wherein the filler material is located in an undercut area of the first number of molded teeth relative to an axis of placement of a dental appliance over the number of teeth. The filler material, for example, can be added to the first number of molded teeth among the set of molded teeth after and/or during formation of the dental mold. For instance, once the dental mold is formed, the filler material can be added over the first number of molded teeth. The filler material can include the same material as the molded teeth and/or a different material. The filler material can create a negative image of the virtual filler on the dental appliance.

In various embodiments of the present disclosure, the method 582 can include adding virtual filler material to the first number of molded teeth among the number of molded teeth of a digital model of the number of teeth to produce the dental mold. For instance, a virtual filler can be added to the digital model of the first number of teeth. The virtual filler can represent the physical filler material to be added. The physical dental mold formed using a rapid prototyping apparatus machine can include the physical filler material located in parts of the undercut areas of the first number of molded teeth, for example.

In accordance with some embodiments of the present disclosure, the method 582 can include creating a smooth transition from the filler material to the first number of molded teeth. The smooth transition can include a smooth transition to a gingival line of the number of molded teeth, for instance.

In various embodiments of the present disclosure, the method 582 can include adding filler material to a region of the dental mold to, for example, reduce retention of the dental appliance in the region. For instance, the region of the dental mold can include one of an anterior region, posterior left region, and/or a posterior right region.

In some embodiments, adding a filler region to a region of the dental mold to reduce retention of the dental appliance can be included in any one of, or any combination of: a method of making a dental mold comprising creating a set of molded teeth from a digital dental model of a number of teeth of a patient and adding a filler material to a first number of the molded teeth among the set of molded teeth, wherein the filler material is located in an undercut area of the first number of molded teeth relative to an axis of placement of a dental appliance over the number of teeth; the method, wherein at least one of the first number of molded teeth further includes at least one of an incisor and bicuspid; and, the method, including creating a smooth transition from the filler material to the number of molded teeth.

In some embodiments, an artificial undercut can be introduced in the event that the undercut area value falls below a minimum threshold. An undercut area of a tooth below a minimum threshold can include an insufficient undercut area. For instance, an artificial undercut can be added to a second number of the molded teeth among the molded teeth, wherein the second number of teeth have an undercut area beyond a minimum threshold (e.g., below the threshold). An undercut area beyond a minimum threshold can include an undercut area of a tooth and/or part of a tooth that is less than a threshold distance from the line parallel to the axis of placement and tangential to the relative height of contour (e.g., minimum threshold distance).

FIG. 5B illustrates an example of a method for filling insufficient undercut areas on a dental mold according to one or more embodiments of the present disclosure. The method 583 can include filling insufficient undercut areas of molded teeth with an artificial undercut. At 585, the method 583 can include creating a set of molded teeth from a digital model of a number of teeth of a patient.

At 587, the method 583 can include adding an artificial undercut to a first number of the molded teeth among the set of molded teeth, wherein the artificial undercut is located in an undercut area of the first number of molded teeth relative to an axis of placement of the dental appliance over the number of teeth. The artificial undercut, as used herein, can include a virtual and/or physical protrusion added to the first number of molded teeth among the number of molded teeth of a digital dental model, and/or virtual and/or physical removal of material from the appliance. For instance, the virtual protrusion can be added to the digital model of the first number of teeth. The virtual protrusion can represent a physical protrusion (e.g., an attachment) to be added. The virtual removal of material can include a representation of material removed from the dental appliance (e.g. the digital model). A virtual and/or physical removal of material from the appliance can include creating a pressure point on the dental appliance. A dental appliance created from the digital model including virtual material removed can include pressure points at the location of the virtually removed material (e.g., located in the undercut areas of the first and/or second number of molded teeth).

The artificial undercut can be added to each of the first number of molded teeth, wherein the artificial undercut of each tooth is within a threshold distance from the line that is defined relative to the one or more axes of placement of the dental appliance. Thereby, the artificial undercut can include a virtual and/or physical protrusion and/or a virtual and/or physical pressure point of the appliance that increases the undercut area of a tooth in at least one dimension until the threshold distance is present to ensure adequate appliance retention.

In various embodiments of the present disclosure, a method for filling undercut areas on a dental mold can include adding filler material to a first number of molded teeth among the set of molded teeth, in addition to adding an artificial undercut to a second number of molded teeth among the set of molded teeth. The first number of molded teeth can include representations of teeth with excessive undercut areas. The second number of molded teeth can include representations of teeth with insufficient undercut areas.

Figure 6A:
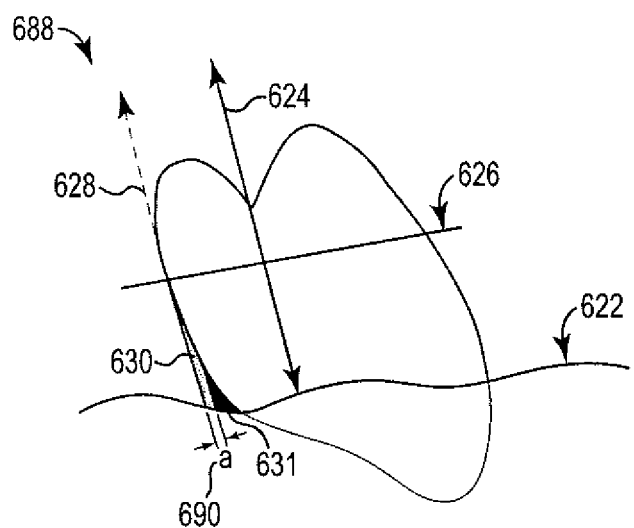
FIG. 6A illustrates an example of a tooth with insufficient undercut area according to one or more embodiments of the present disclosure.

FIG. 6A illustrates an example of a tooth 688 with an insufficient undercut area 630 according to one or more embodiments of the present disclosure. An insufficient undercut area 630 of a tooth 688 can include an undercut area 630 that is not sufficient for retention of a dental appliance.

In accordance with some embodiments of the present disclosure, a tooth 688 can be identified with an insufficient undercut area 630. For example, an insufficient undercut area 630 can be identified by calculating that part of an undercut area 631 relative to a line parallel 628 to an axis of placement 624 is less than a threshold distance from the tooth 688. An insufficient undercut area 630 of the tooth 688 can include an area of the tooth 688 between a height of contour 626 of the tooth 688 relative to an axis of placement 624 of a part of a dental appliance and a gingivia of the tooth 622 (e.g., gum line of the tooth 688).

Part of an undercut area 631 of a tooth may be beyond than the threshold distance from the tooth 688, for instance, if part of the undercut area 631 is closer than the threshold distance to a line parallel 628 to an axis of placement 624 and tangential to the height of contour 626 of the tooth. For example, an undercut area 630 of a tooth 688 may be insufficient if the distance 690 (e.g., distance α) between part of the undercut area 631 of the tooth 688 and the line parallel 628 to an axis of placement 624 is less than the threshold distance (e.g., minimum threshold distance and/or area).

Figure 6B:
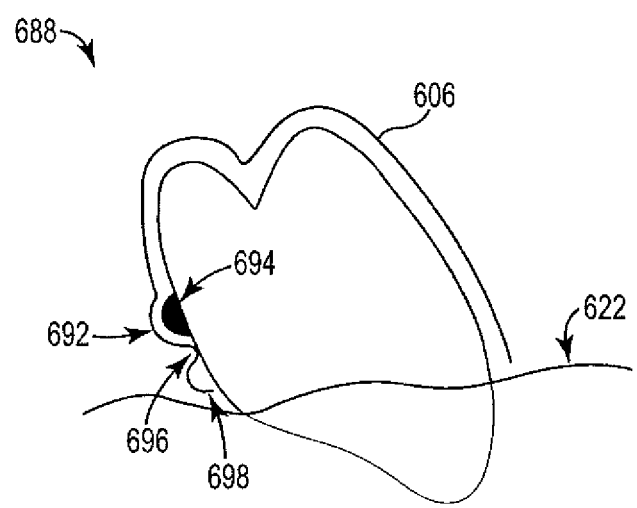
FIG. 6B illustrates an example of a dental appliance according to one or more embodiments of the present disclosure.

FIG. 6B illustrates an example of a dental appliance 606 according to one or more embodiments of the present disclosure. The dental appliance 606 can include an attachment 694 created to retain the dental appliance 606 onto the number of teeth (e.g., tooth 688).

An attachment 694, for instance, can include a ridge 692 on the dental appliance 606 used to retain the dental appliance 606 onto a tooth 688 with an insufficient undercut area (e.g., as illustrated by 630 of FIG. 6A). An attachment 694 can be added, for instance, to create greater retention of a part of the dental appliance 606 in a particular direction (e.g., greater degree of fit of the dental appliance). The appliance 606 can include a physical protrusion 698 extending a surface of the tooth 688 (e.g., lingually).

An attachment 694 can include an apparatus added to the tooth. An attachment 694 can be added to a tooth 688 that has an identified insufficient undercut area. For instance, the attachment 694 can be added directly to the patient's tooth 688. The attachment 694 can include an attachment sub-device with a small base extending across a mesial-distal and/or gingiva-crown of the tooth 688. The attachment 694 can be bonded to any surface of the tooth 688, including a lingual surface which would allow the attachment 694 to be more unnoticeable to others. Shape and design considerations can reduce or prevent any irritation to the contacting tissues, such as the tongue, inner lip, and/or inner cheek. The attachment 694 can be designed to work with a removable dental appliance (e.g., 606). For instance, the attachment 694 can provide friction against a ridge 692 of the dental appliance 606 to increase retention of the dental appliance 606.

The ridge 692, in combination with the attachment 694, may cause the dental appliance 606 to flare from the tooth 688 of the patient. The flare, for instance, can include a hollow space and/or gap (e.g., gap 696) between the gingival line of the patient 622 and an edge of the dental appliance 606 proximal to the gingival line 622 of the patient. Tissue near the flare, such as a tongue, inner lip, and/or inner cheek of a patient, can become trapped in the gap and become inflamed and/or irritated. Thereby, the edge of the appliance can create and/or cause a rough edge on the dental appliance 606 (e.g., edge of the dental appliance proximal to the gingival line of the patient 622).

In accordance with one or more embodiments of the present disclosure, as illustrated by FIG. 6B, a dental appliance 606 with a ridge 692 can include an inward-facing smooth edge 698 from the hollow space and/or gap 696 created by the ridge 692 to the gingiva of a tooth 622 and/or the tooth 688. An inward-facing smooth edge 698 can be created, for example, by creating a smooth transition on a virtual and/or physical dental mold from a hollow space and/or gap 696 caused by a ridge 692 and/or attachment 694 to the molded tooth and/or number of molded teeth (e.g., tooth 688). For instance, a distance of the smooth transition (e.g., smooth edge 698) can be equal and/or proportional to a depth of the ridge 692 (e.g., the depth the ridge 692 protrudes toward a surface of the tooth 688). The smooth edge 698 can reduce and/or prevent discomfort to a patient's mouth (e.g., tongue, lips, and gums), for example, by reducing and/or preventing a rough edge on the dental appliance 606 created and/or caused by the ridge 692 and/or attachment 694. The inward-facing smooth edge 698 can be contoured toward the tooth 688 and/or gums 622, for example.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the above description has been made in an illustrative fashion, and not a restrictive one. Combination of the above embodiments, and other embodiments not specifically described herein will be apparent to those of skill in the art upon reviewing the above description.

The scope of the various embodiments of the disclosure includes any other applications in which the above structures and methods are used. Therefore, the scope of various embodiments of the disclosure should be determined with reference to the appended claims, along with the full range of equivalents to which such claims are entitled.

In the foregoing Detailed Description, various features are grouped together in example embodiments illustrated in the figures for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A non-transitory computing device readable medium having executable instructions that can be executed by a processor to cause a computing device to perform a method, comprising:
   calculating an undercut area of a virtual tooth included in a digital model of a number of virtual teeth relative to an axis of placement of a part of a virtual dental appliance over the number of virtual teeth and a height of contour that is defined based on the axis of placement;
   determining whether the undercut area is less than a minimum threshold distance from the axis of placement, wherein the minimum threshold distance is less than a threshold distance from the virtual tooth, the threshold distance defined relative to the axis of placement and the height of contour; and
   adding a virtual protrusion to the virtual tooth of the number of virtual teeth in response to the undercut area being less than the threshold distance; and
   providing the virtual protrusion for a physical protrusion on a physical dental appliance.

2. The non-transitory computing device readable medium of claim 1, wherein the virtual protrusion is configured to retain the virtual dental appliance onto the number of virtual teeth.

3. The non-transitory computing device readable medium of claim 1, wherein the virtual protrusion is within the threshold distance from a line that is defined relative to the axis of placement of the virtual dental appliance.

4. The non-transitory computing device readable medium of claim 1, wherein the virtual protrusion includes a base.

5. The non-transitory computing device readable medium of claim 1, wherein adding the virtual protrusion to the virtual tooth includes attaching the virtual protrusion to the virtual tooth via a base of the virtual protrusion.

6. The non-transitory computing device readable medium of claim 1, wherein the instructions are executed to add the virtual protrusion to a lingual surface of the virtual tooth.

7. The non-transitory computing device readable medium of claim 1, wherein the instructions are executed to perform the method including creating a ridge in the virtual dental appliance to accommodate the virtual protrusion.

8. The non-transitory computing device readable medium of claim 7, wherein the virtual protrusion is configured to provide friction against the ridge in the virtual dental appliance to retain the virtual dental appliance onto the number of virtual teeth.

9. The non-transitory computing device readable medium of claim 7, wherein the instructions are executed to perform the method including defining an inward-facing smooth edge of the virtual dental appliance proximal to a gingival line of the number of virtual teeth as a result of the creation of the ridge.

10. The non-transitory computing device readable medium of claim 9, wherein the instructions are executed to define the inward-facing smooth edge of the virtual dental appliance to contour towards the virtual tooth.

11. A method of making a dental mold, comprising:
    receiving a digital model of a number of teeth of a patient;
    creating a set of molded teeth from the digital model of the number of teeth of the patient;
    determining whether an undercut area of the set of molded teeth is less than a minimum threshold distance relative to an axis of placement of a dental appliance over a number of molded teeth;
    adding a protrusion to a tooth of the number of molded teeth; and
    creating a physical dental appliance using the number of molded teeth, wherein the physical dental appliance includes a ridge such that the protrusion provides friction against the ridge to retain the physical dental appliance onto the number of molded teeth.

12. The method of claim 11, wherein creating the physical dental appliance includes creating an inward-facing smooth edge of the physical dental appliance, wherein the inward-facing smooth edge is located proximal to a gingival line of the number of molded teeth.

13. The method of claim 12, wherein creating the inward-facing smooth edge includes creating a smooth transition on a physical dental mold.

14. The method of claim 13, wherein the smooth transition is equal to a depth of the ridge of the dental appliance.

15. The method of claim 13, wherein the smooth transition is proportional to a depth of the ridge of the dental appliance.

16. The method of claim 11, wherein the method includes calculating the axis of placement of the dental appliance over the number of molded teeth based upon data of previous placements of dental appliances.

17. A computing device implemented method, comprising:
    calculating multiple undercut areas of a sub-set of teeth of a number of teeth relative to axes of placement of different parts of a dental appliance over the number of teeth;
    determining whether each of the multiple undercut areas are less than a minimum threshold distance relative to each respective axis of placement of each tooth of the sub-set of the number of teeth, wherein each minimum threshold distance is less than a threshold distance from each tooth;
    adding a protrusion to each tooth of the sub-set of the number of teeth; and
    creating a physical dental appliance for the number of teeth, wherein the physical dental appliance includes a ridge such that the protrusion of each tooth provides friction against the ridge to retain the physical dental appliance onto the number of teeth.

18. The method of claim 17, wherein calculating the multiple undercut areas includes calculating undercut areas relative to:
    a first axis of placement of a first part of the dental appliance over the number of teeth and a height of contour that is defined based on the first axis of placement; and
    a second axis of placement of a second part of the dental appliance over the number of teeth and a height of contour that is defined based on the second axis of placement.

19. The method of claim 18, wherein the first axis of placement corresponds to an anterior part of the physical dental appliance and the second axis of placement corresponds to a posterior part of the physical dental appliance.

20. The method of claim 18, wherein the first axis of placement corresponds to an anterior part of the physical dental appliance and the second axis of placement corresponds to one of a posterior left part of the physical dental appliance and a posterior right part of the physical dental appliance.

* * * * *